United States Patent [19]
Auchinleck

[11] Patent Number: 5,730,697
[45] Date of Patent: Mar. 24, 1998

[54] AUTOMATICALLY LOADED SWING BUCKET CENTRIFUGE

[75] Inventor: Geoffrey Fletcher Auchinleck, Vancouver, Canada

[73] Assignee: Automed Corporation, Canada

[21] Appl. No.: 824,253

[22] Filed: Mar. 25, 1997

[51] Int. Cl.[6] .............................. B04B 5/02; B04B 15/00
[52] U.S. Cl. ................................ 494/20; 494/37
[58] Field of Search ............................. 494/10, 16, 20, 494/33, 37, 85; 422/72; 436/45

[56] References Cited

U.S. PATENT DOCUMENTS

| 3,151,073 | 9/1964 | Anthon | 422/72 X |
| 3,635,394 | 1/1972 | Natelson | 494/20 X |
| 3,951,334 | 4/1976 | Fleming et al. | |
| 4,010,892 | 3/1977 | Revillet et al. | |
| 4,208,484 | 6/1980 | Sogi et al. | |
| 4,501,565 | 2/1985 | Piramoon | |
| 4,735,776 | 4/1988 | Yamamoto et al. | 436/45 X |
| 4,927,545 | 5/1990 | Roginski | |
| 5,166,889 | 11/1992 | Cloyd | |
| 5,171,532 | 12/1992 | Columbus et al. | |
| 5,242,371 | 9/1993 | Sato et al. | 422/72 X |
| 5,322,497 | 6/1994 | Kobayashi | 494/20 |
| 5,551,941 | 9/1996 | Howell | |

FOREIGN PATENT DOCUMENTS 535073  5/1973  Switzerland ..................... 494/20

*Primary Examiner*—Charles E. Cooley
*Attorney, Agent, or Firm*—Klarquist Sparkman Campbell Leigh & Whinston, LLP

[57] ABSTRACT

An apparatus and method for loading and unloading of sample tubes contained in sample tube carriers from the buckets of a swing bucket centrifuge wherein the method includes the steps of lifting the buckets off the rotor of the centrifuge, pushing sample tubes contained in sample tube carriers out of the buckets, pushing new sample tubes contained in sample tube carriers into the buckets, and lowering the buckets back on to the rotor of the centrifuge. The buckets are suspended from axially aligned pins which fit into slots on opposite sides of the buckets and include openings in the sides of the buckets to admit sample tubes contained in sample tube carriers. Once the centrifuge rotor has moved a bucket into a defined position, a lifting mechanism raises the bucket from the centrifuge rotor to a position adjacent to a pushing mechanism which can push sample tubes contained in sample tube carriers out of the bucket and can push new sample tubes contained in sample tube carriers into the bucket.

6 Claims, 7 Drawing Sheets

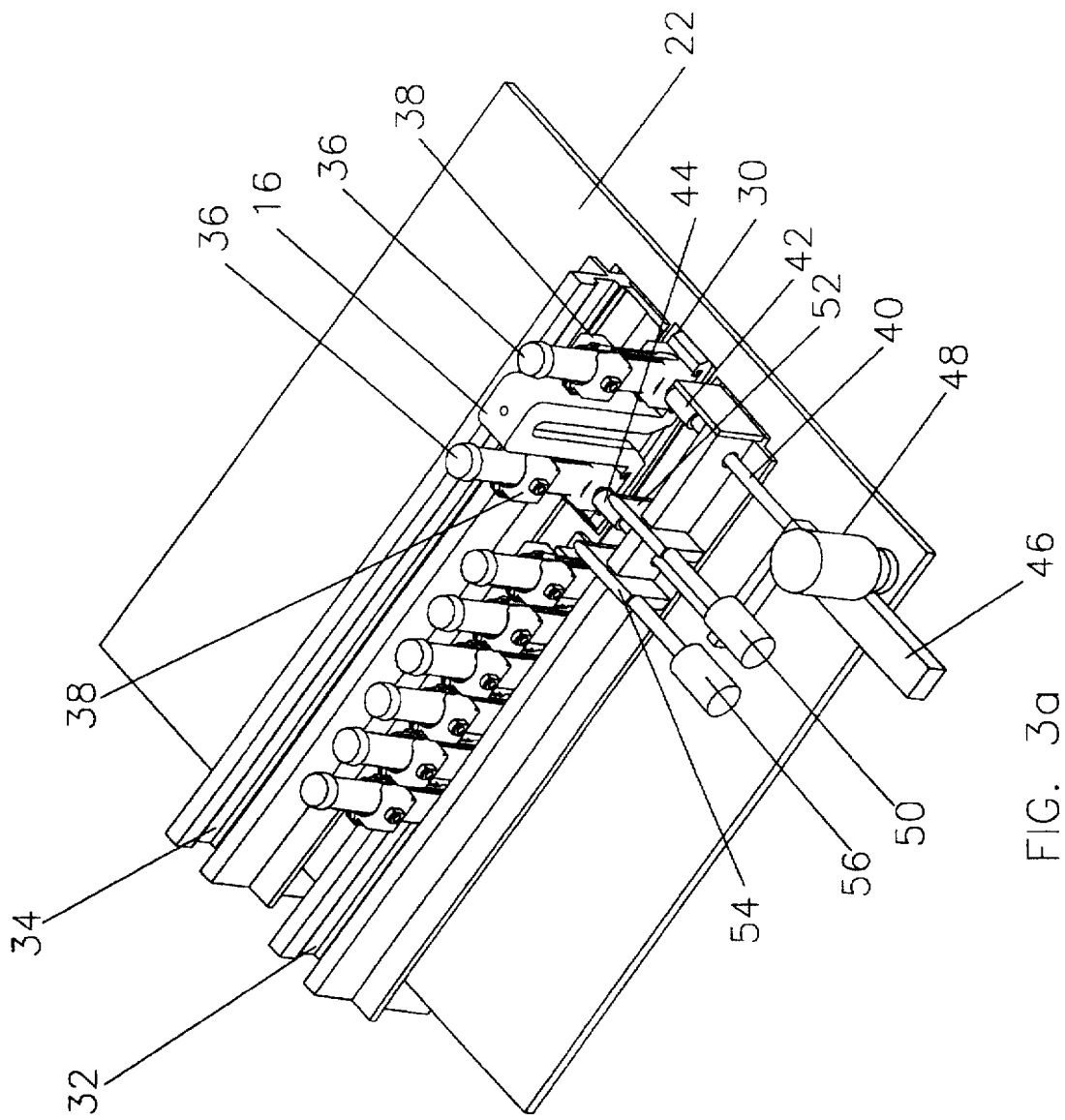

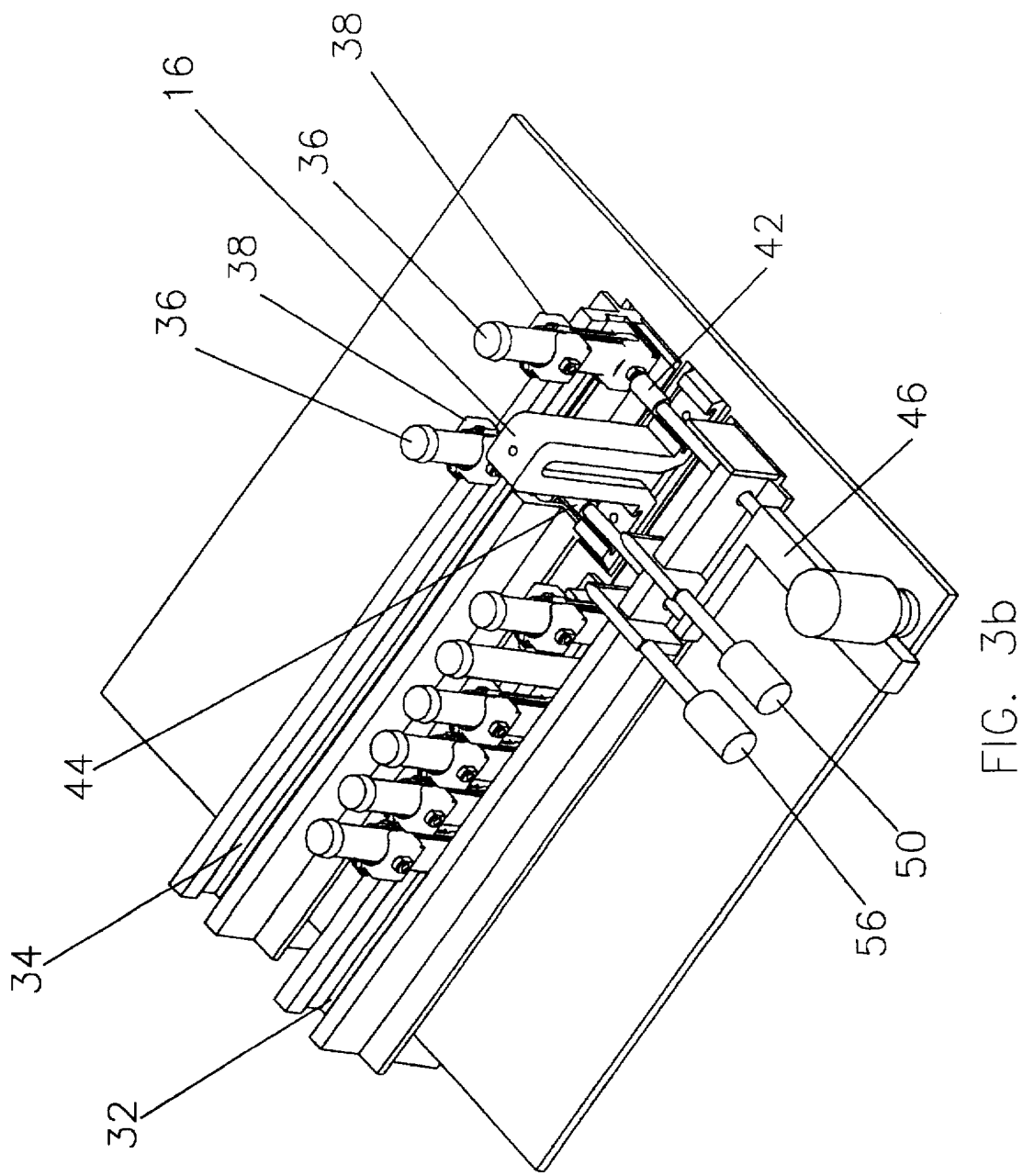

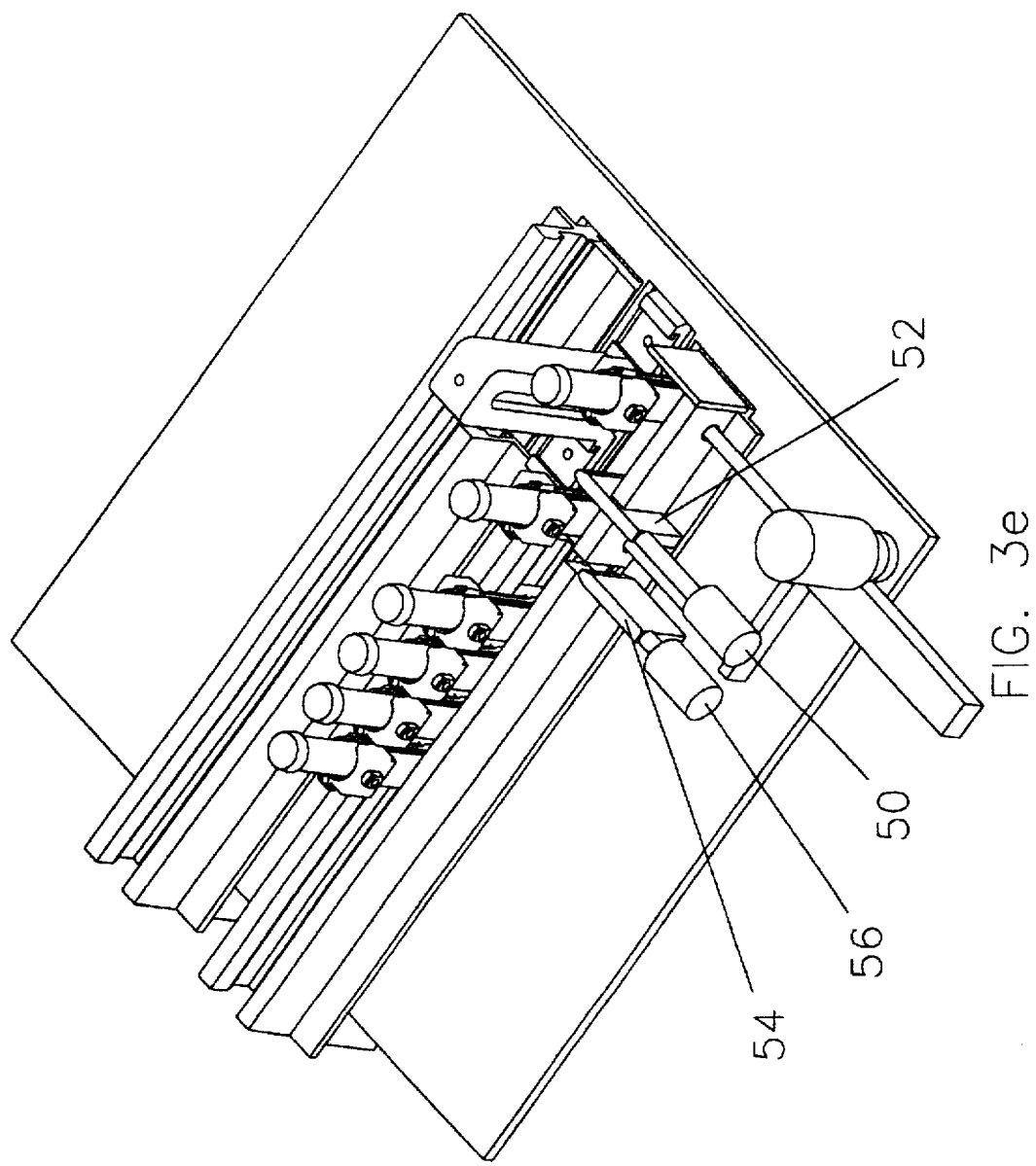

AUTOMATICALLY LOADED SWING BUCKET CENTRIFUGE

FIELD OF THE INVENTION

The current invention relates generally to an automated centrifuge for test tubes. The invention provides a method for automatic loading and unloading of the centrifuge with test tubes contained in carriers. Specifically, the invention provides a method and apparatus for moving test tubes contained in carriers into the buckets of a swing bucket centrifuge by removing the buckets from the centrifuge rotor, moving the test tubes and carriers into the buckets and then replacing the buckets into the centrifuge rotor.

BACKGROUND OF THE INVENTION

During the preparation of blood samples for testing, it is often necessary to centrifuge the blood to separate the blood cells from the serum or plasma so that testing can be done on the serum or plasma. Many centrifuges suitable for this task are known in the art, and can be generally classed as one of two types—either swing bucket or fixed angle. In swing bucket centrifuges, the test tubes are usually placed into holes in a bucket, which is suspended from the centrifuge rotor so that it is free to swing about an axis perpendicular to the axis of rotation of the centrifuge rotor. During operation, the bucket swings about this axis so that the centripetal acceleration created by rotation of the rotor acts along the long axis of the test tube.

In fixed angle centrifuges, the test tubes are usually placed into holes directly in the centrifuge rotor. The holes are typically made at an angle of about 45 degrees to the axis of rotation of the rotor, so that the centripetal acceleration created by the rotation of the rotor acts along an axis at about 45 degrees to the long axis of the test tube.

Centrifuges of both types are typically loaded and unloaded manually, usually by placing individual tubes into holes provided in the buckets in the case of a swing bucket centrifuge, or holes formed directly in the rotor in the case of the fixed angle centrifuge. Manual loading and unloading of samples is undesirable because efficient use of the centrifuge requires that a batch of tubes equal to the number of available locations in the centrifuge be collected before loading is done, thus the task requires attention on a periodic basis, making inefficient use of the operator's time.

Systems intended to automate sample preparation activities in blood testing laboratories, including centrifugation, are now being developed to eliminate such manual, labour intensive activities. As laboratory automation systems usually incorporate means for moving blood samples to and from several preparation steps, it is desirable that an automatically loading centrifuges require no manual intervention at any stage, and that it be amenable to direct and simple connection to other automated machines.

Several approaches to automating all or part of the loading and unloading of centrifuges are known in the art. One such example is described in U.S. Pat. No. 5,551,941 (Howell). In this example, blood sample tubes are manually loaded into a hopper on the top of the machine. Under the influence of gravity, individual tubes are fed into the centrifuge rotor, then, after centrifugation is complete, the tubes can be dropped out the bottom of the rotor. Howell discloses the concept of dropping the tubes directly on to a sample transport system for delivery to other preparatory or analytical steps, but does not explain how samples might be delivered from a sample transport system to the input hopper.

Another approach to automatic loading of a centrifuge is disclosed in U.S. Pat. No. 5,166,889 (Cloyd). In this approach, support wheels are filled with sample containers and are placed directly onto a centrifuge rotor to perform centrifugation. Although the support wheels are moved to and from the centrifuge by a robotic arm, no means for moving the individual samples to and from a sample transport system are disclosed.

In U.S. Pat. No. 4,208,484 (Sogi), a mechanism is disclosed in which blood sample tubes are fed from a delivery system into a tube holder which acts as a swing bucket holding one test tube. The bucket, once loaded with a test tube, is suspended from the centrifuge rotor for centrifugation. After centrifugation is complete, the tube holder is lifted off the centrifuge rotor and inverted to drop the tube out of the tube holder. This system fails to disclose transfer of sample tubes to or from a sample transport system. Inversion of the tube holder to drop the test tube out of the holder would make automatic unloading of the centrifuge difficult, and would, in many cases, cause re-mixing of the centrifuged samples.

The use of robotic arms to load and unload individual tubes from centrifuges is well known in the art, for example, U.S. Pat. No. 4,927,545 (Roginski) and U.S. Pat. No. 4,828,716 (McEwen), the AutoMed AutoFuge (AutoMede Corporation, Richmond, Canada) and others. Although robotic arms provide a flexible means for loading and unloading centrifuge rotors and moving samples to and from sample conveying systems, they are relatively expensive and slow, and as a result have not been widely accepted in laboratories.

SUMMARY OF THE INVENTION

In the present invention, a method and apparatus for automatic loading and unloading of samples from a swing bucket centrifuge are disclosed. The method comprises the steps of lifting a centrifuge bucket from pins on a centrifuge rotor from which it is suspended, to a position above the centrifuge rotor, pushing uncentrifuged samples contained in one or more sample carriers out of the bucket, pushing centrifuged samples contained in one or more sample carriers into the bucket, and lowering the bucket back on to the pins on the centrifuge rotor. The process is repeated for each centrifuge bucket, and the samples are centrifuged by spinning the centrifuge rotor.

The invention includes open sided centrifuge buckets intended to be suspended from a centrifuge rotor, the open sides permitting the loading of samples in carriers by moving the samples laterally into and out of the bucket. Further, each bucket has a chamfered lower edge, so that when the bucket is lifted from the centrifuge rotor by a lifting mechanism it engages a mating chamfered opening in a platform located above the centrifuge rotor such that bucket is in a precisely defined location in the platform. The invention also includes means for pushing one or more sample carriers out of the bucket on to a sample transportation mechanism, and means for pushing one or more sample carriers into the bucket from a sample transportation mechanism.

Another aspect of the invention includes the use of multiple buckets on one centrifuge rotor, the buckets sharing a common lifting, unloading and loading mechanism, wherein each bucket is located beneath the opening in the plate in turn by rotating the centrifuge rotor to a predetermined location. A further aspect of the invention includes buckets which can be loaded with more than one sample during each loading cycle.

In another aspect, the invention includes a mechanism for loading and unloading the centrifuge buckets with a minimum number of actuators and ensuring that the bucket stays correctly oriented during the lifting motion.

BRIEF DESCRIPTION OF THE DRAWING

FIGS. 3a-3e show pictorial views of the centrifuge of FIG. 1 from above the plane of the rotor during each step of the unloading and loading cycle.

DESCRIPTION OF THE PREFERRED EMBODIMENT

Figure 1:
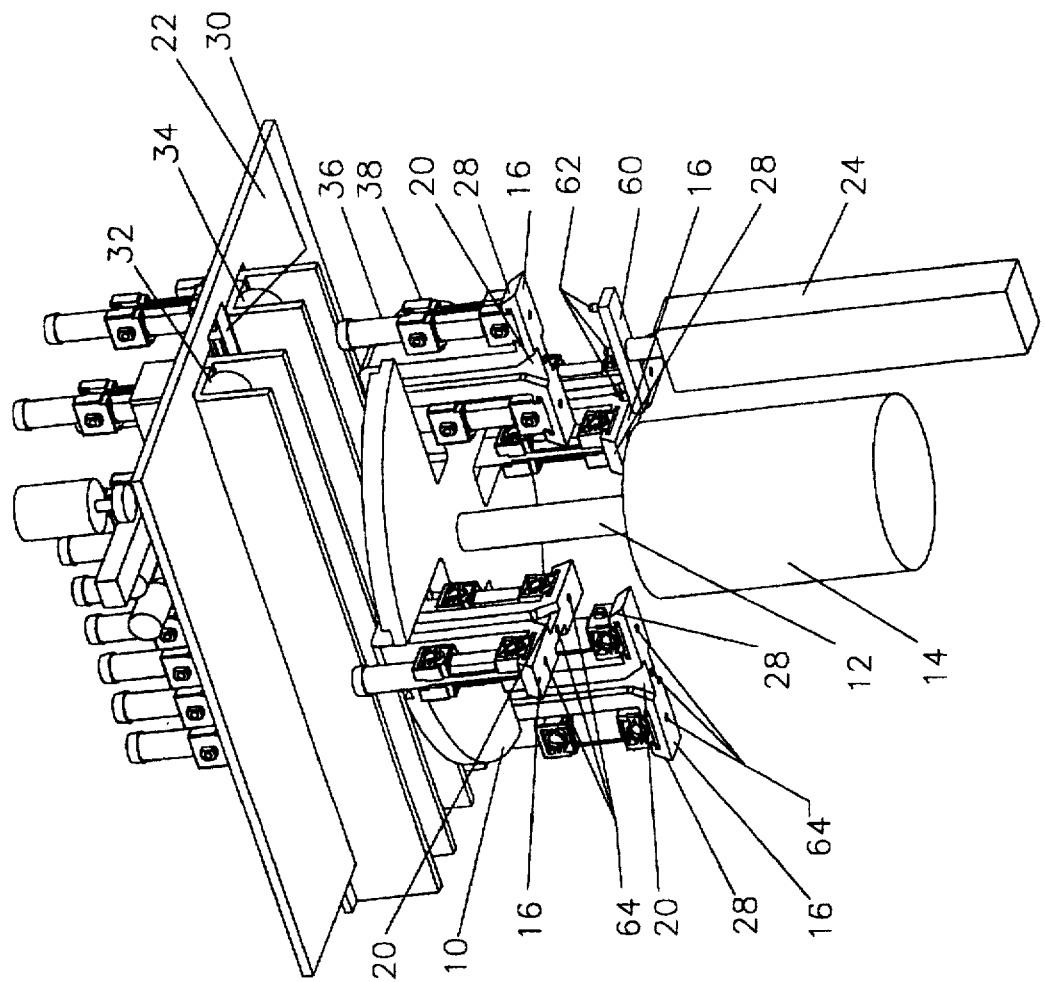
FIG. 1 shows a pictorial view of the centrifuge according to the invention, viewed from below the plane of the rotor.

FIG. 1 shows a pictorial view of a centrifuge according to the invention. Wires, hoses, mounting brackets and the like are not depicted unless specifically relevant to the invention, as the use and application of such components are deemed obvious to one skilled in the art.

Figure 2:
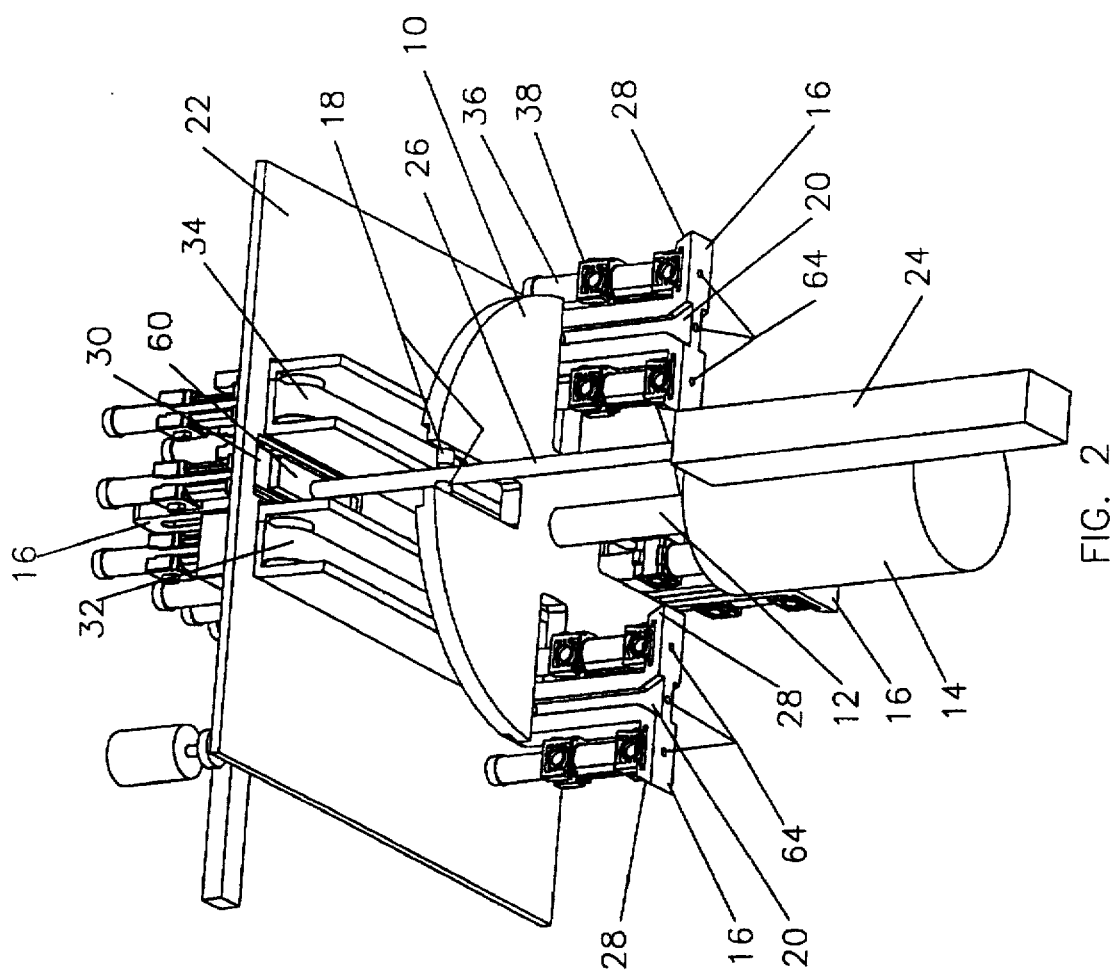
FIG. 2 shows the centrifuge of FIG. 1 with one bucket moved to the loading position.

Centrifuge rotor 10 is attached to shaft 12 of servo motor 14. Servo motor 14 can be made to rotate rotor 10 about the axis of shaft 12 to any angular position and can spin rotor 10 at speeds suitable for creating a desired centripetal acceleration in centrifuge buckets 16. Rotor 10 provides four notches 19 that define locations for suspending centrifuge buckets 16 on pins 18 (not visible in FIG. 1). A pair of pins 18 is carried by the rotor in each notch. Each pin 18 protrudes inwardly into the notch near the peripheral edge of the rotor 10. The two pins 18 are axially aligned, and the outermost ends of the pins are spaced apart. The pins engage slots 20 on each side of buckets 16. The slots are closed at the top but open at the bottom of the buckets, so that the buckets can hang and swing about the pins at the top of the slot and be removed from the pins by lifting the bucket from the pins. In FIG. 2, one bucket 16 is shown lifted to the loading and unloading location in a top platform 22. Bucket 16 is lifted into place by lifting cylinder 24, which in the preferred embodiment is a pneumatic cylinder.

In operation, servo motor 14 moves rotor 10 into position so that a rotor notch 19 and one bucket 16 is directly below opening 30 in top platform 22. Compressed air is introduced into cylinder 24 to cause the end of cylinder rod 26 to engage the bottom of bucket 16 and lift it off of pins 18. Attached to the end of cylinder rod is alignment plate 60 on which are located alignment pins 62. Alignment pins 62 (visible in FIG. 1) engage tapered holes 64 in the underside of the bucket 16 to ensure that the bucket 16 does not rotate relative to the rod 26 while being lifted off pins 18. Bucket 16 is raised until the chamfered base 28 of the bucket 16 engages a mating chamfered opening 30 of top platform 22. The chamfering eliminates any slight misalignment between the bucket and opening as they are moved into engagement. The compressed air in cylinder 24 holds bucket 16 firmly in place in top platform 22 while the loading and unloading of bucket 16 take place.

Referring to FIG. 3a, when mated with opening 30 of top platform 22, bucket 16 is located adjacent to the input belt 32 and output belt 34 of the top platform 22. Sample tubes 36 in carriers 38 may be unloaded from bucket 16 directly on to output belt 34 by pusher mechanism 40. In the preferred embodiment, carriers 38 are Specimen Transport Carriers (AutoMed Corporation, Richmond, British Columbia, Canada), but other carriers could be used equally well. Although buckets 16 used in the preferred embodiment each hold two Specimen Transport Carders, alternative embodiments of buckets 16 could be made to hold any number of carriers of any type.

Pusher mechanism 40 consists of slide 46 moved by stepper motor 48 with a rack and pinion drive. Attached to slide 46 are push rods 42 and 44. In the position shown in FIG. 3a, the ends of push rods 42 and 44 are located next to one face of each of the two sample tube carriers 38 in bucket 16. To unload the carriers 38 from bucket 16, slide 46 is extended so that push rods 42 and 44 push both carriers 38 out of bucket 16 and onto output belt 34, as shown in FIG. 3b. Continuously operating output belt 34 moves both carriers 38 away from the centrifuge.

Figure 3C:
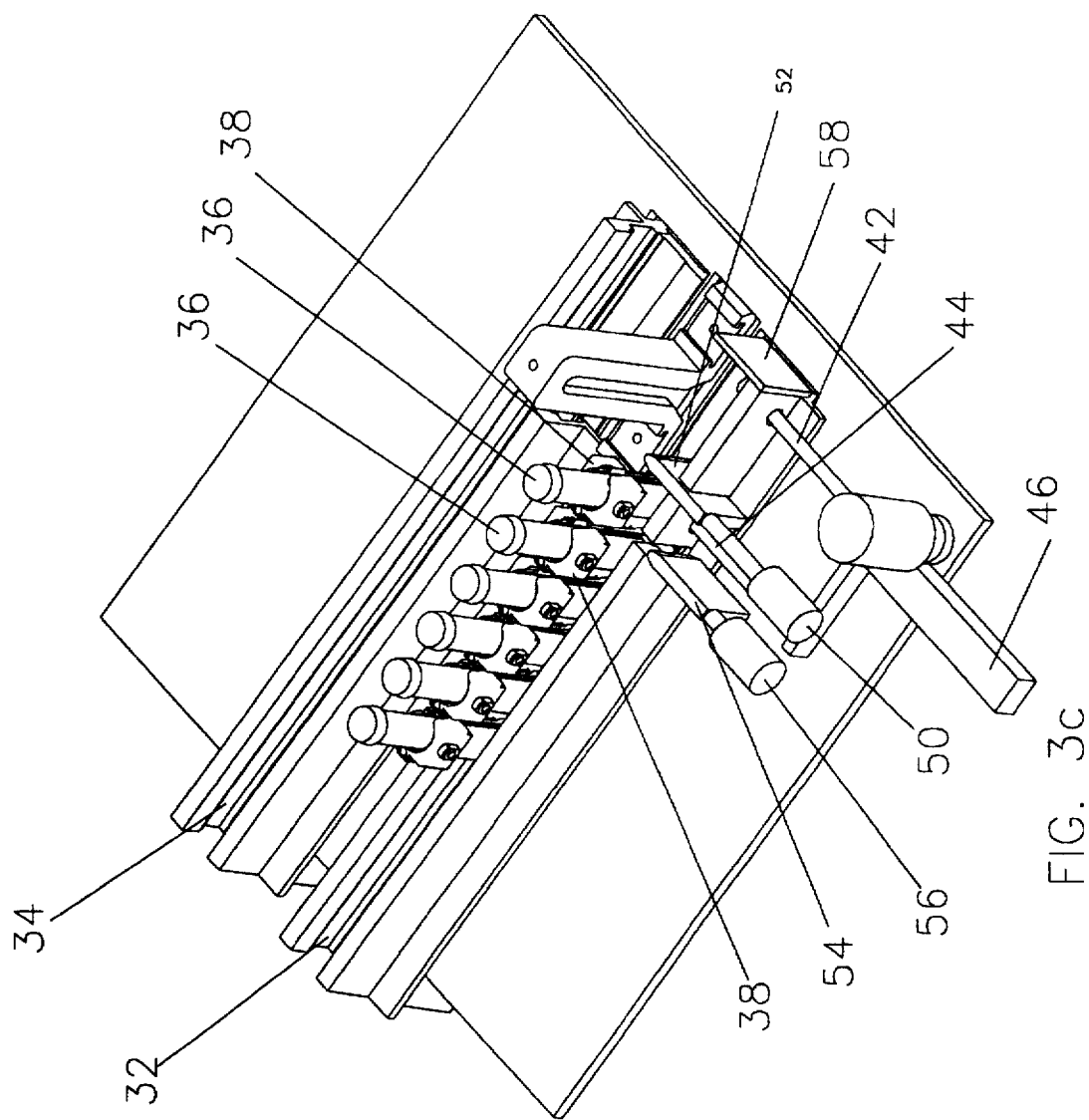
Figure 3D:
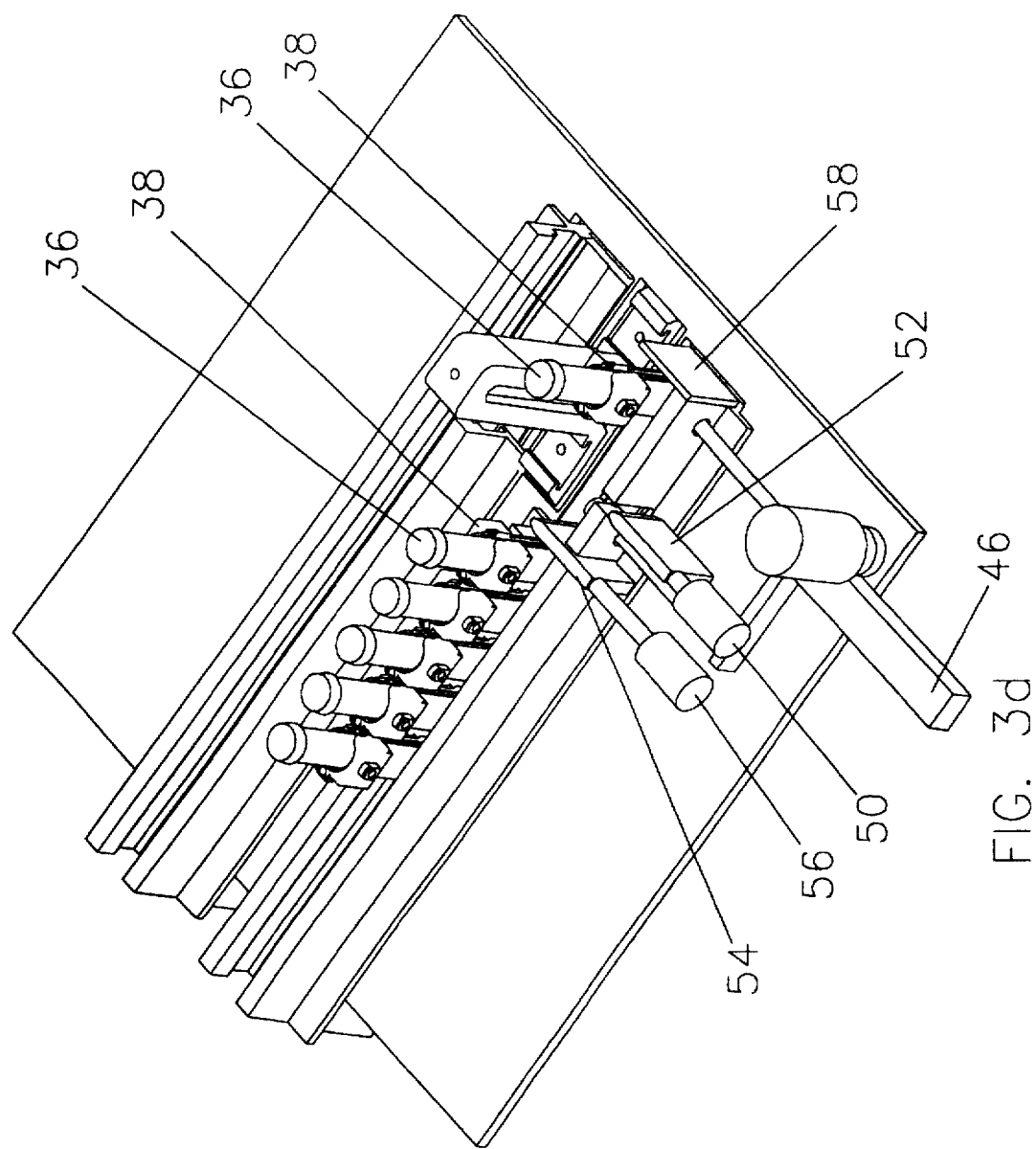

To load new sample tube carriers 38 into bucket 16, slide 46 is retracted so that the ends of push rods 42 and 44 no longer obstruct input belt 32 and solenoid 56 is activated to retract gate 54. Belt 32, which operates continuously, moves the next available carrier 38 until it rests against gate 52, as shown in FIG. 3c. Solenoid 56 is deactivated to extend gate 54, and solenoid 50 is then activated to retract gate 52 to allow the carrier 38 to move to end stop 58 as shown in FIG. 3d. Solenoid 50 is then deactivated and solenoid 56 is activated again to allow another carrier 38 to come to rest against gate 52 as shown in FIG. 3e. Solenoid 56 is then deactivated to extend gate 54 to hold any additional carriers 38 which may be queued on input belt 32 in place. At this stage, two carriers 38 are now positioned on input belt 32 adjacent to bucket 16. To load bucket 16, slide 46 is extended to cause push rods 42 and 44 to push the carriers 38 into bucket 16. Finally, slide 46 is retracted slightly to return the ends of push rods 42 and 44 to their original position. Bucket 16 may now be lowered back onto pins 18 of rotor 10 by releasing the compressed air in cylinder 24, which in the preferred embodiment is of a spring return type. To unload and reload the remaining three buckets of rotor 10, the sequence is repeated.

The foregoing description of the preferred embodiment of the invention has been presented for the purposes of illustration and description. The description is not intended to limit the invention to the form disclosed, consequently, variations and modifications to the embodiment described, within the skill and knowledge of the relevant art, are within the scope of the present invention. The embodiment described here is further intended to explain the best mode presently known of practicing the invention and to enable others skilled in the art to utilize the invention as such, or other embodiments, and with the various modifications required by their particular application or uses of the invention. It is intended that the appended claims be construed to include alternative embodiments.

I claim:

1. A method for loading and unloading sample tube carriers from the buckets of a swing bucket centrifuge, comprising the steps of:

lifting a bucket from the rotor of the centrifuge to a pre-determined location;

pushing sample tube carriers out of the bucket to unload the bucket;

pushing sample tube carriers into the bucket to load the bucket; and lowering the bucket on to the rotor of the centrifuge.

2. Apparatus for automatically loading a centrifuge with sample tube carriers, comprising:

a centrifuge rotor having a pair of spaced apart pins located about its edge;

a centrifuge bucket which may be suspended from the pair of pins such that the bucket may swing about the pins and be lifted off the pins, wherein the bucket has openings on opposite sides to permit the loading and unloading of one or more sample carriers onto the bucket;

a lifting means for lifting the bucket off the pins to a pre-determined location and for lowering the bucket back onto the pins from the pre-determined location;

an input transport means for moving sample tube carriers to a position adjacent to the bucket when the bucket is lifted to the pre-determined location;

an output transport means for moving sample carriers away from a position adjacent to the bucket when the bucket is lifted to the pre-determined location; and a pushing mechanism for pushing sample carriers out of the bucket and into the output transport means and for pushing sample carriers into the bucket from the input transport means.

3. The apparatus of claim 2 in which the lifting means includes a plate member that engages the underside of the bucket so as to prevent rotation of the bucket with respect to the plate member while the bucket is being lifted.

4. The apparatus of claim 2 further including a platform having a chamfered opening located at the pre-determined location to engage a mating chamfer on the bucket to eliminate misalignment between the bucket and the pre-determined location when the lifting mechanism moves the bucket to the pre-determined location.

5. The apparatus of claim 2 in which the pins are of circular cross section.

6. The apparatus of claim 2 in which the pins engage slots formed in opposite sides of the bucket, the slots being closed at one end so that the bucket can be suspended from the pins and can be lifted vertically off the pins.

* * * * *